US010123955B2

(12) United States Patent
Brooks

(10) Patent No.: US 10,123,955 B2
(45) Date of Patent: Nov. 13, 2018

(54) MALODOUR COUNTERACTING COMPOSITIONS

(71) Applicant: Givaudan, S.A., Vernier (CH)

(72) Inventor: Matthew Peter Brooks, Canterbury (GB)

(73) Assignee: Givaudan, S.A., Vernier (CH)

( * ) Notice: Subject to any disclaimer, the term of this patent is extended or adjusted under 35 U.S.C. 154(b) by 0 days.

(21) Appl. No.: 15/480,697

(22) Filed: Apr. 6, 2017

(65) Prior Publication Data

US 2017/0209353 A1 Jul. 27, 2017

Related U.S. Application Data

(63) Continuation of application No. 14/002,014, filed as application No. PCT/EP2012/055073 on Mar. 22, 2012.

(30) Foreign Application Priority Data

Mar. 22, 2011 (GB) .................................. 1104766.9

(51) Int. Cl.
| | |
|---|---|
| *A61K 8/41* | (2006.01) |
| *A61K 8/362* | (2006.01) |
| *A61L 9/014* | (2006.01) |
| *C11B 9/00* | (2006.01) |
| *A61Q 15/00* | (2006.01) |
| *A61K 8/37* | (2006.01) |
| *A61L 9/01* | (2006.01) |
| *A61Q 13/00* | (2006.01) |

(52) U.S. Cl.
CPC .............. *A61K 8/416* (2013.01); *A61K 8/362* (2013.01); *A61K 8/37* (2013.01); *A61L 9/01* (2013.01); *A61L 9/014* (2013.01); *A61Q 13/00* (2013.01); *A61Q 15/00* (2013.01); *C11B 9/0019* (2013.01); *A61L 2209/21* (2013.01); *A61L 2209/22* (2013.01)

(58) Field of Classification Search
CPC .......... A61K 8/416; A61K 8/362; A61K 8/37; A61L 9/014; A61L 9/01; A61L 2209/22; A61L 2209/21; C11B 9/0019; A61Q 15/00; A61Q 13/00
See application file for complete search history.

(56) References Cited

U.S. PATENT DOCUMENTS

| | | |
|---|---|---|
| 3,077,457 A | 2/1963 | Kulka |
| 4,822,602 A | 4/1989 | Sabatelli |
| 5,565,525 A | 10/1996 | Morimoto et al. |
| 5,766,578 A | 6/1998 | Davis |
| 6,020,287 A | 2/2000 | Brinker et al. |
| 6,093,691 A | 7/2000 | Sivik et al. |
| 6,610,648 B2 | 8/2003 | McGee et al. |
| 2002/0165133 A1 | 11/2002 | Kim et al. |
| 2005/0226821 A1 | 10/2005 | Waugh et al. |
| 2008/0032912 A1 | 2/2008 | Warr et al. |
| 2008/0299054 A1 | 12/2008 | Chandar et al. |
| 2010/0111889 A1* | 5/2010 | Marsh .................. A61K 8/0208 424/76.1 |
| 2010/0209378 A1 | 8/2010 | Flachsmann et al. |

FOREIGN PATENT DOCUMENTS

| | | |
|---|---|---|
| CN | 101249095 A | 8/2008 |
| EP | 2524704 A2 | 11/2012 |
| GB | 1432163 A | 4/1976 |
| JP | S4942837 A | 4/1974 |
| JP | S54113440 A | 9/1975 |

(Continued)

OTHER PUBLICATIONS

PCT/EP2012/055073—International Search Report, dated Oct. 22, 2012.
PCT/EP2012/055073—International Written Opinion, dated Oct. 22, 2012.
PCT/EP2012/055073—International Preliminary Report on Patentability, dated Sep. 24, 2013.
GB 1104766.9—Search Report, dated Jul. 8, 2011.
Chan, et al., "Nucleophile-Initiated Thiol-Michael Reactions: Effect of Organocatalyst, Thiol and Ene", Macromolecules, Jul. 14, 2010, pp. 6381-6386, vol. 43, Issue 15. Abstract Only.
Ingalsbe, et al., "Development of a novel expression, ZIMAX/KZI, for determination of the counter-anion effect on the antimicrobial activity of tetrabutylammonium salts", Biorganic & Medicinal Chemistry Letters, Sep. 1, 2009, pp. 4984-4987, Vo;. 19, Issue 17. Abstract Only.
Ranu, et al., "A Simple, Efficient, and Green Procedure for the 1,4-Addition of Thiols to Conjugated Alkenes and Alkynes Catalyzed by Sodium Acetate in Aqueous Medium", Australian Journal of Chemistry, Apr. 2, 2007, pp. 223-227, vol. 60, Issue 3. Abstract only.

(Continued)

*Primary Examiner* — Trevor Love
(74) *Attorney, Agent, or Firm* — Curatolo Sidoti Co., LPA; Joseph G. Curatolo; Salvatore A. Sidoti

(57) ABSTRACT

A malodor-counteracting composition comprising
(i) a salt of general formula (I)

$$R_1R_2R_3R_4N^+X^- \qquad (I)$$

wherein $R_1$, $R_2$, $R_3$, $R_4$ are independently selected from $C_{1-4}$ alkyl, or $R_1$, $R_2$, $R_3$, $R_4$ may together constitute a nitrogen-containing cyclic system in which the nitrogen is part of a pyridinium or an imidazolinium ring; and $X^-$ is a counterion characterized by its protonated form having an acidity constant (pKa) lying between 1 and 6; and
(ii) an alpha, beta-unsaturated carbonyl compound of the general formula $$R_5R_6C=CR_7C(=O)YR_8 \qquad (II)$$

wherein $R_5$, $R_6$, $R_7$ and $R_8$ are independently selected from hydrogen and $C_{1-10}$ hydrocarbyl residues which may be saturated, unsaturated, aromatic, cyclic, branched or unbranched, and are optionally substituted, or $R_5$, $R_6$, $R_7$ and $R_8$ may together constitute a cyclic system and Y is oxygen or a single covalent bond, with the proviso that Y is a covalent bond when $R_8$ is hydrogen. The composition may be incorporated into consumer products and is able to remove malodors from the air or from surfaces.

24 Claims, No Drawings

(56) References Cited

FOREIGN PATENT DOCUMENTS

| JP | S5231832 A | 3/1977 |
| JP | H0538358 A | 2/1993 |
| JP | 2010537749 A | 12/2010 |
| JP | 2011246377 A | 12/2011 |
| WO | WO 02/13776 A2 | 2/2002 |
| WO | WO 02/051788 A1 | 7/2002 |
| WO | WO 02/064106 A1 | 8/2002 |
| WO | WO 03/072039 A2 | 9/2003 |

OTHER PUBLICATIONS

Ranu, et al., "Catalysis by an ionic liquid: efficient conjugate addition of thiols to electron deficient alkenes catalyzed by molten tetrabutylammonium bromide under solvent-free conditions", Tetrahedron, Mar. 31, 2003, pp. 2417-2421, vol. 59, Issue 14. Abstract Only.
Viso, et al., Tetrabutylammonium acetate, Encyclopedia of Reagents for Organic Synthesis, 2001, p. 1.

\* cited by examiner

MALODOUR COUNTERACTING COMPOSITIONS

CROSS REFERENCE TO RELATED APPLICATIONS

This application is a continuation of U.S. application Ser. No. 14/002,014 having a 371(c) date of Sep. 18, 2012, which is a national stage application of International Application No. PCT/EP2012/055073, filed 22 Mar. 2012, which claims priority from Great Britain Patent Application No. 1104766.9, filed 22 Mar. 2011, which applications are incorporated herein by reference.

This disclosure relates to malodour counteracting compositions, to methods of using these compositions and to perfumes incorporating them.

The problem of malodours has been with mankind for as long as civilization. There are very few articles or things which do not have some odour associated with them. Often this odour is undesirable, such as tobacco smoke odour, cooking odours, and odours of, e.g. mould, bathroom and pets. The compounds that cause malodour are often highly volatile, and are encountered in the air, as well as on substrates such as fabric, hard surfaces, skin and hair.

Many fragrance compositions merely mask undesirable odours with a stronger, desirable odour. The malodorant molecules survive the presence of perfume.

There are several routes to reducing malodour, for example by using absorbers, such as sodium bicarbonate, activated charcoal, zinc ricinoleate, zeolites, cyclodextrins, etc. These compositions are only partially effective and they have the disadvantage of removing both malodour and fragrance.

Other approaches to reducing malodour that have been proposed include chemical neutralization, reducing or eliminating the partial vapor pressure of the malodour in air.

While all of the approaches set forth above are designed to mitigate malodors, none of them are free from defects, such as inadequate elimination of the malodor, or taking too long to provide a malodour benefit, leading to unacceptable performance.

It has now been found that the addition of specific quaternary ammonium salts to alpha, beta-unsaturated esters, aldehydes and ketones may significantly improve their ability to remove malodour from the air. There is therefore provided a malodour-counteracting composition comprising (i) a salt of general formula (I)

$$R_1R_2R_3R_4N^+X^- \quad (I)$$

wherein $R_1$, $R_2$, $R_3$, $R_4$ are independently selected from $C_{1-4}$ alkyl, or $R_1$, $R_2$, $R_3$, $R_4$ may together constitute a nitrogen-containing cyclic system in which the nitrogen is part of a pyridinium or an imidazolinium ring; and $X^-$ is a counterion characterised by its protonated form having an acidity constant (pKa) lying between 1 and 6; and (ii) an alpha, beta-unsaturated carbonyl compound of the general formula

$$R_5R_6C=CR_7C(=O)YR_8 \quad (II)$$

wherein $R_5$, $R_6$, $R_7$ and $R_8$ are independently selected from hydrogen and $C_{1-10}$ hydrocarbyl residues which may be saturated, unsaturated, aromatic, cyclic, branched or unbranched, and are optionally substituted, or $R_5$, $R_6$, $R_7$ and $R_8$ may together constitute a cyclic system and Y is oxygen or a single covalent bond, with the proviso that Y is a covalent bond when $R_8$ is hydrogen.

There is additionally provided a method of counteracting malodour in the atmosphere or on a substrate, comprising the application to the atmosphere or substrate of a composition as hereinabove described.

Non-limiting examples of compounds according to the formula I (hereinafter "Compound I") include tetrabutylammonium acetate (CAS No: 10534-59-5) and tetraethylammonium benzoate (CAS No: 16909-22-1). The acidity constant (pKa) of the protonated counterion is particularly between 2 and 5, more particularly between 3 and 5.

The optional substituents of the compound of Formula II (hereinafter "Compound II") include hydroxy, alkoxy, keto, alkoxycarbonyl, carbalkoxy and ether.

Particular embodiments of Compound II are those wherein
 (a) $R_7$ is hydrogen and Y is absent; and
 (b) at least one of $R_5$ and $R_6$ is an ester group and Y is an oxygen atom, such that the compound is a di-ester or tri-ester.

Non-limiting examples of Compound II include citral, cinnamaldehyde and damascone.

The weight ratio of Compound I to Compound II advantageously lies within the range 1:1000 to 1:5, particularly between 1:500 to 1:20, and more particularly 1:300 to 1:30.

The malodour-counteracting compositions may also contain other adjuncts known in the art, for example solvents such as glycols and glycol ethers, preservatives such as parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; organic acids, such as sorbic acid, benzoic acid, and their salts; anti-oxidants and/or UV screens such as pentaerythritol tetrakis(3-(3,5-di-tert-butyl-4-hydroxyphenyl)propionate), 2,6-di(ter.butyl)-4-methylphenol, 2-ethylhexyl para-methoxycinnamate; stabilizers/chelants such as ethylenediaminetetracetates, pentetic acid, etidronic acid, diethylenetriaminepentaacetates, and ethylenediamine disuccinate.

One embodiment of the disclosure comprises malodour-absorbing perfume containing at least 0.075% w/w of at least one Compound II, together with at least one Compound I, Compound I being selected such that its solubility in the perfume is at least 100 ppm by weight at 25° C., particularly at least 200 ppm. In a further particular embodiment, there is present in the perfume at least 0.1% w/w, particularly 0.25% w/w, more particularly 0.5%. w/w, more particularly 2% w/w, based on the perfume of at least one Compound II.

For the purposes of this application, a perfume is regarded as a mixture of odiferous perfume ingredients as described in standard texts such as "Perfume and Flavour Materials", by Steffen Arctander (Montclair, N.J., 1969) published in two volumes, "Perfume and Flavor Materials of Natural Origin", S. Arctander (Elizabeth, N.J., 1960), together with solvents such as diethyl phthalate, dipropylene glycol, isopropyl myristate, triethyl citrate, and glycol ethers such as carbitol, and those sold under the 'Dowanol' brand (e.g. Dowanol DPM, Dowanol TPM, Dowanol DPnP, Dowanol DPMA etc.). In general the water content of a perfume is usually below 1%, more typically under 0.3%, and often below 0.1%, and this tends to limit dramatically the solubility of salts within perfume.

In a particular low-odour embodiment, Compound II comprises a fumarate (i.e. a di-ester of trans-butane-1,4- dioic acid). Certain fumarates such as dihexyl fumarate are known as counteractants of nucleophilic malodorants, for example amines and thiols (U.S. Pat. No. 6,610,648 and U.S. Pat. No. 3,077,457). It has been found that a combination with Compound I with such a fumarate has a significantly enhanced malodour reduction capability, in some cases an order of magnitude better than known compositions. A particular combination is a mixture of at least one of tetrabutylammonium acetate and tetraethylammonium benzoate with dihexyl fumarate in a ratio of from 1:300 to 1:30.

Another aspect of the disclosure concerns a method for removing malodour from the air, comprising treatment of the air directly or indirectly, the latter via the treatment of a substrate such as a hard surface, fabric, hair or skin in contact with the air, comprising the exposure to the air or the application to a substrate of a consumer product incorporating an effective amount of a malodour-counteracting composition as hereinabove defined. The malodour-counteracting composition may be added directly into the consumer product or incorporated via a perfume as described herein.

The compositions of the present invention may be incorporated into various products, e.g., consumer products, such as for example the products set forth in more detail below. There is therefore also provided a consumer product, comprising a consumer product base and an effective amount of a malodour-counteracting composition as hereinabove described.

As used herein, "consumer products" include, for example products designed for personal care, as well as more functional products directed towards fabrics, hard surfaces, toilets, and air fresheners. Suitable products applied to the skin may include, for example, talcum powder, deodorants and antiperspirants in the form of sprays, soft solids, and solids, lotions, and oils, and soap, syndet, and combination soap and syndet personal wash bars, personal wash liquids, and personal wipes. Products for the hair encompass for example, shampoos, conditioners, styling sprays, mousses, gels, hair wipes, hair sprays, and hair pomades. Household products include fabric washing liquids and powders, fabric conditioners, wipes, dishwashing liquids and powders, hard surface cleaning liquids and powders, and aqueous and non-aqueous sprays. The term 'air fresheners' may include, for example, sprays, candles, gels, plug-in electrical devices, battery-operated and other forms of vapour dispensing devices for introducing compositions into spaces, and liquid wicking systems.

By "consumer product base" is meant the totality of all of the ingredients needed to prepare a consumer product, apart from the malodour-counteracting composition. These will naturally vary depending on the nature of the composition, but they are no different in kind and proportion from those known and used in the art.

As used herein, an "effective amount" of the composition, e.g., consumer product, will vary depending upon the intended use, the composition used, the ambient conditions, and other well known variables. Using the examples provided below, one skilled in the art may judge the appropriate amounts of the malodour reducing compositions to be used in order to dispense an effective amount of, e.g. the consumer product, into the space. The table below summarises the amounts of compounds I and II which are suitable for a representative range of consumer products.

|  | Typical Concentration Ranges % | | |
| --- | --- | --- | --- |
| Product | Perfume | Compound I | Compound II |
| Air freshener (aerosol) | 0.3-1.5 | 0.0001-0.002 | 0.003-0.15 |
| Air Freshener (liquid electrical) | to 100* | 0.002-0.1 | 0.5-5 |
| Liquid rim-block (toilet care) | 2-10 | 0.0002-0.05 | 0.025-2 |
| Fragranced candles | 1-10 | 0.0001-0.002 | 0.01-0.1 |
| Hard surface cleaners | 0.2-1 | 0.0003-0.002 | 0.002-0.1 |
| Underarm deodorants | 0.5-3 | 0.0001-0.001 | 0.01-0.1 |
| Fabric conditioners | 0.25-1.5 | 0.0005-0.005 | 0.02-0.15 |

*A "liquid electrical" is a device that releases fragrance into an atmosphere with the aid of electrical heating. The fragrances generally contain variable proportions of solvent. The 100% perfume figure includes these.

The disclosure is now further described with reference to the following non-limiting examples, which depict particular embodiments.

EXAMPLE 1

Synthesis of dihexyl 2-(propylsulfanyl)succinate (A1)

A reference sample of the 1,4-adduct A1 generated between dihexyl fumarate (DHF) and propanethiol was prepared as follows.

Lithium carbonate (100 mg, 1.35 mmol), dihexyl fumarate (0.5 g, 1.76 mmol) and ethanol (4.5 g, 5.7 mL) were placed into a round bottom flask along with a magnetic stirrer bar and sealed. Propanethiol (180 µL, 2.0 mmol) was added to the suspension and the progress of the reaction was monitored by gas chromatography using aliquots of the reaction mixture (10 µL) diluted in ethyl acetate (1 mL). After the reaction had reached equilibrium the suspension was filtered (0.2 µm) and the resulting solution was reduced using a rotary evaporator (yield of Adduct A1 ca.100%). NMR and mass spectroscopic analyses confirmed the presence of the desired adduct.

EXAMPLE 2

Effect of tetrabutylammonium acetate on the reaction between dihexyl fumarate (DHF) and propanethiol Propanethiol volatile malodorant typical of many mercaptans found in nature, and is conveniently monitored by gas chromatography.

Propanethiol (100 microliter) was added to a dilution (9%) of dihexyl fumarate in one of two commercial perfumes (ca. 0.6 g in total) at 22° C. and the system left undisturbed for 15 minutes. An aliquot was removed and diluted in ethyl acetate prior to analysis by gas chromatography, and the extent of adduct formation was measured (as a percentage). The experiment was repeated with small amounts (0.2% w/w) of the salt tetrabutylammonium acetate (TBAA) present.

After 15 minutes no adduct was detectable in the absence of the salt. The results shown in Table 1 indicate that TBAA greatly increases the formation of the DHF-thiol adduct even when diluted extensively in perfume.

Other quaternary ammonium salts with counterions from stronger acids (pKa<1) such as Tetrabutylammonium methosulfate, tetrabutylammonium bromide and tetramethylammonium bromide gave no detectable product after the 15 minutes incubation.

TABLE 1

Formation of Adduct A1 in the liquid phase

| Sample | TBAA % | Perfume | % Reaction Progress (after 15 min) |
|---|---|---|---|
| 1 | 0 | 1 | 0.0% |
| 2 | 0.2 | 1 | 6.3% |
| 3 | 0 | 2 | 0.0% |
| 4 | 0.2 | 2 | 4.7% |

EXAMPLE 3

Effect of tetrabutylammonium acetate (TBAA) on the scavenging of propanethiol from air by dihexyl fumarate (DHF)

The ability of dihexyl fumarate to remove thiol from the air in contact with a liquid phase sample was assessed by standard headspace gas chromatography (HGC). Liquid samples (0.5 g) were placed in headspace vials (of volume 20 mL) which were sealed using magnetic caps fitted with PTFE septa. Hexadecane (a chemically inert liquid) was used as a control. It is anticipated that the only mechanism removing thiol from the headspace above hexadecane samples is physical solubilisation. A gas phase malodour challenge (propanethiol, 1 ml of saturated vapour above neat propanethiol at 30° C.) was injected automatically (via a Gerstel MPS 2XL autosampler fitted to an HP 7890 gas chromatograph) into each vial which was then incubated (with agitation) at 40° C. for 30 minutes. Removal of propanethiol from the headspace (scavenging) was measured using headspace gas chromatography. The results were expressed in terms of headspace reduction (HSR) compared to that of hexadecane, as indicated in the following equation:

HSR=(control malodour peak area−sample malodour peak area)/(control malodour peak area)

The HSRs are shown in Table 2.

TABLE 2

Headspace reduction of Propanethiol by systems comprising 90% dihexyl fumarate together with quaternary salt TBAA (0.01% or 0.1% w/w) and solvent (balance).

| Sample No. | Salt | Salt Conc. | Solvent | RSD | Reduction |
|---|---|---|---|---|---|
| 1 | none | — | — | <10% | 20% |
| 2 | TBAA | 0.01% | DDPM | 10% | 33% |
| 3 | TBAA | 0.01% | BA | 5% | 37% |
| 4 | TBAA | 0.10% | MMB | 6% | 97% |
| 5 | TBAA | 0.01% | MMB | 1% | 37% |
| 6 | TBAA | 0.10% | EtOH | 11% | 97% |

Key: DDPM = Dowanol DPM
BA = benzyl alcohol
MMB = 3-methoxyl-3-methylbutanol
EtOH = ethanol

The invention claimed is:

1. A malodour-counteracting composition comprising
(i) a salt selected from tetrabutylammonium acetate, tetrabutylammonium benzoate and tetraethylammonium benzoate; and
(ii) an alpha, beta-unsaturated carbonyl compound comprising a fumarate, in which the fumarate comprises dihexyl fumarate, wherein the malodour is a thiol malodour, and
wherein the weight ratio of the salt to that of the alpha, beta-unsaturated carbonyl compound is from 1:1000 to 1:5.

2. The composition according to claim 1, wherein the salt comprises tetrabutylammonium acetate.

3. The composition according to claim 1, in which the weight ratio of the salt to that of the alpha, beta-unsaturated carbonyl compound is from 1:1000 to 1:20.

4. The composition according to claim 1, in which the weight ratio of the salt to that of the alpha, beta-unsaturated carbonyl compound is from 1:500 to 1:20.

5. The composition according to claim 1, in which the weight ratio of the salt to that of the alpha, beta-unsaturated carbonyl compound is from 1:300 to 1:30.

6. The composition according to claim 5, in which the salt is at least one of tetrabutylammonium acetate, tetrabutylammonium benzoate and tetraethylammonium benzoate; the alpha, beta-unsaturated carbonyl compound is dihexyl fumarate; and the weight ratio of the salt to dihexyl fumarate is from 1:300 to 1:30.

7. A consumer product, comprising a consumer product base and an effective amount of a malodour-counteracting composition according to claim 1.

8. A malodour-absorbing perfume containing at least 0.075% w/w, based on the perfume, of at least one alpha, beta-unsaturated carbonyl compound comprising dihexyl fumarate, together with at least one salt selected from tetrabutylammonium acetate, tetrabutylammonium benzoate and tetraethylammonium benzoate having a solubility in the perfume of at least 100 ppm by weight at 25° C., where the malodour is a thiol malodour, and
wherein the weight ratio of the salt to that of the alpha, beta-unsaturated carbonyl compound is from 1:300 to 1:30.

9. The perfume of claim 8, wherein the solubility in the perfume of the salt is at least 200 ppm by weight at 25° C.

10. The perfume of claim 8, containing at least 0.1% w/w, based on the perfume, of at least one alpha, beta-unsaturated carbonyl compound.

11. A method of counteracting malodour in the atmosphere or on a substrate, comprising the application to the atmosphere or substrate of the composition according to claim 1, wherein the malodour is a thiol malodour.

12. A method for removing malodour from the air, comprising treatment of the air directly or indirectly, the latter via the treatment of a substrate comprising a hard surface, fabric, hair or skin in contact with the air, the method comprising the exposure to the air or the application to a substrate of a consumer product incorporating an effective amount of a malodour-counteracting composition according to claim 1.

13. A malodour-counteracting composition comprising
(i) a salt selected from tetrabutylammonium acetate, tetraethylammonium benzoate, and tetrabutylammonium benzoate; and
(ii) an alpha, beta-unsaturated carbonyl compound comprising citral, damascone, ethyl decadienoate, or nonadienal,
wherein the malodour is a thiol malodour, and
wherein the weight ratio of the salt to that of the alpha, beta-unsaturated carbonyl compound is from 1:1000 to 1:5.

14. The malodour-counteracting composition of claim 13, wherein the salt is selected from tetrabutylammonium acetate and tetrabutylammonium benzoate.

15. The malodour-counteracting composition of claim 13, wherein the salt comprises tetrabutylammonium benzoate.

16. A consumer product, comprising a consumer product base and an effective amount of the malodour-counteracting composition according to claim 13.

17. A method of counteracting malodour in the atmosphere or on a substrate, comprising the application to the atmosphere or substrate of the composition according to claim 13.

18. A method for removing malodour from the air, comprising treatment of the air directly or indirectly, the latter via the treatment of a substrate comprising a hard surface, fabric, hair or skin in contact with the air, the method comprising the exposure to the air or the application to a substrate of a consumer product incorporating an effective amount of a malodour-counteracting composition according to claim 13.

19. A malodour-absorbing perfume containing at least 0.075% w/w, based on the perfume, of at least one alpha, beta-unsaturated carbonyl compound comprising citral, damascone, ethyl decadienoate, or nonadienal, together with at least one salt selected from tetrabutylammonium acetate, tetraethylammonium benzoate, and tetrabutylammonium benzoate having a solubility in the perfume of at least 100 ppm by weight at 25° C., where the malodour is a thiol malodour, and wherein the weight ratio of the salt to that of the alpha, beta-unsaturated carbonyl compound is from 1:300 to 1:30.

20. The perfume of claim 19, wherein the solubility in the perfume of the salt is at least 200 ppm by weight at 25° C.

21. The perfume of claim 19, containing at least 0.1% w/w, based on the perfume, of the at least one alpha, beta-unsaturated carbonyl compound.

22. The malodour-counteracting composition of claim 13, in which the weight ratio of the salt to that of the alpha, beta-unsaturated carbonyl compound is from 1:1000 to 1:20.

23. The malodour-counteracting composition of claim 13, in which the weight ratio of the salt to that of the alpha, beta-unsaturated carbonyl compound is from 1:500 to 1:20.

24. The malodour-counteracting composition of claim 13, in which the weight ratio of the salt to that of the alpha, beta-unsaturated carbonyl compound is from 1:300 to 1:30.

* * * * *